United States Patent [19]
Fischetti et al.

[11] Patent Number: 6,056,955
[45] Date of Patent: May 2, 2000

[54] TOPICAL TREATMENT OF STREPTOCOCCAL INFECTIONS

[76] Inventors: Vincent Fischetti, 488 Joan Ct., West Hempstead, N.Y. 11552; Lawrence Loomis, 11374 Buckleberry Path, Columbia, Md. 21044

[21] Appl. No.: 09/395,637

[22] Filed: Sep. 14, 1999

[51] Int. Cl.⁷ .................................................. A61K 38/43
[52] U.S. Cl. ...................... 424/94.1; 424/450; 424/78.03; 424/443; 424/45; 424/94.61; 514/2; 514/937; 514/948; 514/944
[58] Field of Search .................................. 424/94.1, 450, 424/78.03, 443, 45, 94.61; 514/2, 937, 948, 944

[56] References Cited

U.S. PATENT DOCUMENTS 5,985,271  11/1999  Fischetti et al. ....................... 424/94.1
5,997,862  12/1999  Fischetti et al. ....................... 424/94.1

*Primary Examiner*—Raj Bawa
*Attorney, Agent, or Firm*—Jonathan Grant, Grant Patent Services

[57] ABSTRACT

The present invention discloses a method and composition for the topical treatment of streptococcal infections by the use of a lysin enzyme blended with a carrier suitable for topical application to dermal tissues. The method for the treatment of dermatological streptococcal infections comprises administering a composition comprising effective amount of a therapeutic agent, with the therapeutic agent comprising a lysin enzyme produced by group C streptococcal bacteria infected with a C1 bacteriophage. The therapeutic agent can be in a pharmaceutically acceptable carrier.

49 Claims, No Drawings

TOPICAL TREATMENT OF STREPTOCOCCAL INFECTIONS

BACKGROUND OF THE INVENTION

1. Field of the Invention

The present invention discloses a method and composition for the topical treatment of streptococcal infections by the use of a lysin enzyme blended with a carrier suitable for topical application to dermal tissues.

2. Description of the Prior Art

The genus Streptococcus is comprised of a wide variety of both pathogenic and commensal gram-positive bacteria which are found to inhabit a wide range of hosts, including humans, horses, pigs, and cows. Within the host, streptococci are often found to colonize the mucosa surfaces of the mouth, nares and pharynx. However, in certain circumstances, they may also inhabit the skin, heart or muscle tissue.

Pathogenic streptococci of man include *S. pyogenes, S. pneumoniae,* and *S. faecalis.* While Group A streptococci can be present in the throat or on the skin and cause no symptoms of disease, they may also cause infections that range from mild to sever and even life-threatening. Among the pathogenic hemolytic streptococci, *S. pyogenes,* or group A streptococci have been implicated as the etiologic agent of acute pharyngitis "(strep throat"), impetigo, rheumatic fever, scarlet fever, glomerulonephritis, and invasive fasciitis. Necrotizing fasciitis (sometimes described by the media as "the flesh-eating bacteria") is a destructive infection of muscle and fat tissue. Invasive group A streptococcal infections occur when the bacteria get past the defenses of the person who is infected. About 10,000 to 15,000 cases of invasive GAS disease occur in the United States each year resulting in over 2,000 deaths. CDC estimates that 500 to 1,500 cases of necrotizing fasciitis and 2,000 to 3,000 cases of streptococcal toxic shock syndrome occur each year in the United States. Approximately 20% of patients with necrotizing fasciitis die, and 60% of patients with streptococcal toxic shock syndrome die. About 10 to 15% of patients with other forms of invasive group A streptococcal disease die.

Additionally, Group C Streptococcus can cause cellulitis from skin breaks, although cellulitis is normally associated with Staphylococcus aureus. Cellulitis can result in death, particularly in older individuals or in individuals who are already weakened.

The first individual to identify the serological and immunological groups of streptococci was Dr. Rebecca Lancefield, (Lancefield, R. C., "A Serological Differentiation of Human and other Groups of Hemolytic Streptococci," J. Exp. Med., Vol.57, pp 571–595 1933), after whom the grouping system was named. The group A streptococcus was identified on the basis of B-1, 4 N-acetylglucosamine terminal sugar moieties on a repeating rhamnose sugar backbone found as part of the structure of the organism's cell wall. Antiserum raised against group A streptococci and subsequent absorptions to remove cross-reactions were shown to specifically react with the cell wall component of these organisms and became the grouping antisera for group A streptococci. A number of methods have been devised to fragment the group A streptococcal cell wall carbohydrate. These methods include heating by boiling at pH 2.0, autoclaving, trichloroacetic acid extraction, hot formamide digestion, nitrous acid extraction and enzyme digestion by enzymes derived from the soil microorganisms of species streptomyces, and the phage-associated enzyme lysin. Each of these methods have various advantages and disadvantages.

The rapid diagnosis of group A streptococcal pharyngitis has become more readily available to both physicians and clinical laboratories by replacing time consuming culturing methods requiring a minimum of 24 to 72 hours to identify the presence of group A streptococci with a rapid antigen-antibody test capable of being performed and read in less than one hour. Culturing methods vary in the degree of sensitivity of detection. In one case, a simple 5% sheep blood agar plate may be used in conjunction with a Bacitracin disc and culturing 24 hours at 37 degree(s) C. aerobically to identify group A streptococci. Alternatively, selective media and anaerobic conditions may be used to inhibit overgrowth by other organisms and incubation at 35 degree (s) C. for a minimum of 48 hours. In addition, depending on the transport media, the delay in testing, and any antibacterial agents that the patient may have taken, culturing may result in nonviable organisms that fail to grow in the media although the patient is indeed colonized by the group A streptococcus. In the latter case a sensitive immunoassay for group A streptococcal antigen can detect these nonviable organisms.

In the past, antibiotics were used to treat Streptococcal infections. U.S. Pat. No. 5,260,292 (Robinson et al.) discloses the topical treatment of acne with aminopenicillins. The mouth and composition for topically treating acne and acneiform dermal disorders includes applying an amount of an antibiotic selected from the group consisting of ampicillin, amoxicillin, other aminopenicillins, and cephalosporins, and derivatives and analogs thereof, effective to treat the acne and acneiform dermal disorders.

U.S. Pat. No. 5,409,917 (Robinson et al.) discloses the topical treatment of acne with cephalosporins.

Neither of these applications specifically call for the treatment of streptococcal infections, nor do they address the problems of streptococcal cellulitis or necrotizing fasciitis. Additionally, the use of these antibiotics are presenting new problems. Specifically, a growing number of people are allergic to penicillin, one of the primary antibiotics used to treat Streptococcal infections. Even when penicillin can be used, penicillin resistant strains of Staphylococcal aureus which may be present in the organism can produce penicillinase, which can destroy the penicillin before it has time to act on the Streptococcus. Erythramycin can be used to treat Streptococcal infections; however, 20–30% of Streptococcus are resistant to erythramycin. Also, it is hypothesized that some streptococcus can lie dormant for up to ten days; cells which are not reproducing will not be killed by traditional antibiotics.

Consequently, other efforts have been sought to first identify and then kill Streptococcus.

Maxted, (Maxted, W. R., "The Active Agent in Nascent Phage Lysis of Streptococci," J. Gen Micro, vol 16, pp 585–595 1957), Krause, (Krause, R. M., "Studies on the Bacteriophages of Hemolytic Streptococci," J. Exp Med, vol 108, pp 803–821, 1958), and Fischetti, (Fischetti, V. A., et al, "Purification and Physical Properties of Group C Streptococcal Phage Associated Lysin," J. Exp Med, Vol 133 pp 1105–1117 1971), have reported the characteristics of an enzyme produced by the group C streptococcal organism after being infected with a particular bacteriophage identified as C1. The enzyme was given the name lysin and was found to specifically cleave the cell wall of group A, group C and group E streptococci. These investigators provided information on the characteristics and activities of this enzyme with regard to lysing the group A streptococci and releasing the cell wall carbohydrate. They never reported on the utility of this enzyme in an immunological diagnostic test for the detection of group A streptococci from throat swabs in patients. The failure to use this enzyme for a clinical diagnostic test was due to a number of problems associated with the enzyme such as: the difficulty in growing large amounts of bacteriophage in the group C streptococci, the time delays in inactivating the residual enzyme when trying to obtain phage stocks, the instability of the enzyme itself to oxidative conditions and heat, and nonspecific reactions in immunoassays performed in the presence of other organisms and the biological components in the sample.

U.S. Pat. No. 5,604,109 (Fischetti et al.) teaches the rapid and sensitive detection of group A streptococcal antigens by a diagnostic test kit which utilizes a sampling device consisting of a throat swab made of synthetic or natural fibers such as Dacron or rayon and some type of shaft which holds the fibers, is long enough to place the fibers in the tonsillar area and is capable of being used to swab the area to remove sufficient numbers of colonizing or infecting organisms. The swab can then be placed in the enzyme extraction reagent and subsequently used in an immunoassay. The invention can comprise a test kit for detecting Group A streptococci, containing the lysin enzyme for releasing Group A streptococcal components, and a ligand capable of binding with a component of the Group A streptococcus.

U.S. patent (application Ser. No. 08/962,523) (Fischetti, et. al.) and U.S. patent (application Ser. No. 09/257,026) (Fischetti et al.) disclose the use of an oral delivery mode, such as a candy, chewing gum, lozenge, troche, tablet, a powder, an aerosol, a liquid or a liquid spray, containing a lysin enzyme produced by group C streptococcal bacteria infected with a C1 bacteriophage for the prophylactic and therapeutic treatment of Streptococcal A throat infections, commonly known as strep throat.

None of the prior art suggests the use of the lysin enzyme for the treatment of topical or dermatological infections.

SUMMARY OF THE INVENTION

The present invention (which incorporates U.S. Pat. No. 5,604,109, and U.S. patent application Ser. No. 09/257,026 (Fischetti et al.) and U.S. patent application Ser. No. 08/962, 523 (Fischetti) in their entirety by reference) is a composition containing uses a therapeutic agent which comprises the lysin enzyme produced by the group C streptococcal organism after being infected with a particular bacteriophage (identified as C1) for application to the streptococcal infected dermatological part of the body as a method to fight a streptococcal infection, particularly those infections, such as impetigo, which result in invasive fascfitis, necrotizing fasciitis, and the streptococcal form of cellulitis. Based upon the discovery that phage lysin can effectively and efficiently break down the cell walls of Group A Streptococci, with the resultant antigenic fragments being reactive with antibodies specific for the Group A Streptococcal carbohydrate, the composition is particularly useful as a therapeutic treatment of Streptococcal dermatological infections. The semipurified enzyme lacks proteolytic enzymatic activity and therefore is non-destructive to specific antibodies when present during the digestion of the bacterial cell wall. Treatment of group A streptococci with dilute samples of lysin results in the removal of the organism's protective cell wall by the enzyme, thereby killing the strep organism. The treatment of streptococci in biological fluids in vivo has the same effect.

In one embodiment of the invention, the lysin enzyme would be administered in the form of a topical ointment or cream. In another embodiment of the invention, the lysin enzyme would be administered in an aqueous form.

In yet another embodiment of the invention, lysostaphin, the enzyme which lyses Staphylococcus aureus, can be included in the therapeutic agent. In a further embodiment of the invention, conventional antibiotics may be included in the therapeutic agent with the lysin enzyme, and with or without the presence of lysostaphin. Other bacterial lysing enzymes may also be included in the therapeutic agent.

DETAILED DESCRIPTION OF THE INVENTION

Treatment of group A streptococci with dilute samples of lysin results in the removal of the organism's protective cell wall by the enzyme, thereby killing the strep organism. The presence of the lysin on a dermatological tissue when streptococci are present results in the killing of the streptococci, thus cutting short the invasive process and further skin and tissue damage. This rapid and specific (lethal) activity of the lysin enzyme against streptococcus will have a profound beneficial effect by killing even "dormant" cells, which are not killed by conventional antibiotics, which rely upon the cells reproducing in order to kill the bacteria.

The amidase muralytic (lysin) enzyme produced by the group C streptococcal organism after being infected with a particular bacteriophage (identified as C1) is isolated and harvested as is described in U.S. patent application Ser. No. 5,604,109. This Group C streptococcal enzyme, (also known as a lysin enzyme) which has unique specificity for the cell wall of groups A, C, and E Streptococci, may alternatively be isolated and harvested by any other known means.

The composition which may be used for the therapeutic treatment of a strep dermatological infection includes the lysin enzyme and, preferably, a mode of application (such as a carrier), to the skin or tissue, such that the enzyme is put in the carrier system which holds the enzyme on the skin.

Prior to, or at the time the enzyme is put in the carrier system, it is preferred that the enzyme be in a stabilizing buffer environment for maintaining a pH range between about 4.0 and about 8.0, more preferably between about 5.5 and about 7.5 and most preferably at about 6.1.

The stabilizing buffer should allow for the optimum activity of the lysin enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate-phosphate buffer.

To prevent spoilage, the stabilizing buffer may further contain a bactericidal or bacteriostatic reagent as a preservative, such as a small amount of sodium benzoate.

The mode of application for the lysin enzyme includes a number of different types and combinations of carriers which include, but are not limited to an aqueous liquid, an alcohol base liquid,, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes but is not limited to a smear, spray, a time-release patch, a liquid absorbed wipe, and combinations thereof.

More specifically, the carriers of the compositions of the present invention may comprise semi-solid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations which can aid in the exposure of the skin to a medicament.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL.RTM." (B.F. Goodrich, Cleveland, Ohio), "HYPAN.RTM.1" (Kingston Technologies, Dayton, N.J.), "NATROSOL.RTM." (Aqualon, Wilmington, Del.), "KLUCEL.RTM." (Aqualon, Wilmington, Del.), or "STABILEZE.RTM." (ISP Technologies, Wayne, N.J.). Preferably, the gelling agent comprises between about 0.2% to about 4% by weight of the composition. More particularly, the preferred compositional weight percent range for "CARBOPOL.RTM." is between about 0.5% to about 2%, while the preferred weight percent range for "NATROSOL.RTM." and "KLUCEL.RTM." is between about 0.5% to about 4%. The preferred compositional weight percent range for both "HYPAN.RTM." and "STABILEZE.RTM." is between about 0.5% to about 4%.

"CARBOPOL.RTM." is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL.RTM." is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

Pharmaceuticals for use in all embodiments of the invention include antimicrobial agents, anti-inflammatory agents, antiviral agents, local anesthetic agents, corticosteroids, destructive therapy agents, antifungals, and antiandrogens. In the treatment of acne, active pharmaceuticals that may be used include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone acetonide, betamethasone valerate, triamcinolone acetonide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Destructive therapy agents such as salicylic acid or lactic acid may also be used. A concentration of about 2% to about 40% by weight is preferred. Cantharidin is preferably utilized in a concentration of about 5% to about 30% by weight. Typical antifungals that may be used in this invention and their preferred weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). For the topical treatment of seborrheic dermatitis, hirsutism, acne, and alopecia, the active pharmaceutical may include an antiandrogen such as flutamide or finasteride in preferred weight percentages of about 0.5% to 10%.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

In one embodiment, the invention comprises a dermatological composition having about 0.5% to 10% carbomer and about 0.5% to 10% of a pharmaceutical that exists in both a dissolved state and a microparticulate state. The dissolved pharmaceutical has the capacity to cross the stratum corneum, whereas the microparticulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. A preferred ratio of micro particulate to dissolved dapsone is five or less.

In another embodiment, the invention comprises about 1% carbomer, about 80–90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL.RTM. 980" and the caustic material may include sodium hydroxide solution.

In a preferred embodiment, the composition comprises dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL.RTM." gelling polymer, methylparaben, propylparaben, titanium dioxide, BHA, and a caustic material to neutralize the "CARBOPOL.RTM.."

Any of the carriers for the lysin enzyme may be manufactured by conventional means. However, if alcohol is used in the carrier, the enzyme should be in a micelle, liposome, or a "reverse" liposome, to prevent denaturing of the enzyme. Similarly, when the lysin enzyme is being placed in the carrier, and the carrier is, or has been heated, such placement should be made after the carrier has cooled somewhat, to avoid heat denaturation of the enzyme. In a preferred embodiment of the invention, the carrier is sterile.

The enzyme may be added to these substances in a liquid form or in a lyophilized state, whereupon it will be solubilized when it meets a liquid body.

The effective dosage rates or amounts of the lysin enzyme to treat the infection, and the duration of treatment will depend in part on the seriousness of the infection, the duration of exposure of the recipient to the Streptococci, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 100 units/ml to about 500,000 units/mil of composition, preferably in the range of about 1000 units/ml to about 100,000 units/ml, and most preferably from about 10,000 to 100,000 units/ml. The amount of active units per ml and the duration of time of exposure depends on the nature of infection, and the amount of contact the carrier allows the lysin enzyme to have. It is to be remembered that the enzyme works best when in a fluid environment. Hence, effectiveness of the enzyme is in part related to the amount of moisture trapped by the carrier. In another preferred embodiment, a mild surfactant in an amount effective to potentiate the therapeutic effect of the lysin enzyme. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

In order to accelerate treatment of the infection, and to treat any non-Streptococcus bacteria, the therapeutic agent may further include at least one complementary agent which can also potentiate the bactericidal activity of the lysin enzyme. The complementary agent can be penicillin, synthetic penicillins bacitracin, methicillin, cephalosporin, polymyxin, cefaclor. Cefadroxil, cefamandole nafate, cefazolin, cefixime, cefinetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefiroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef, mafate, chelating agents and any combinations thereof in amounts which are effective to synergistically enhance the therapeutic effect of the lysin enzyme.

Additionally, the therapeutic agent may further comprise the enzyme lysostaphin for the treatment of any Staphylococcus aureus bacteria. Mucolytic peptides, such as lysostaphin, have been suggested to be efficacious in the treatment of S. aureus infections of humans (Schaffter et al., Yale J. Biol. & Med., 39:230 (1967) and bovine mastitis caused by S. aureus (Sears et al., J. Dairy Science, 71 (Suppl. 1): 244(1988)). Lysostaphin, a gene product of Staphylococcus simulans, exerts a bacteriostatic and bactericidal effect upon S. aureus by enzymatically degrading the polyglycine crosslinks of the cell wall (Browder et al., Res. Comm., 19: 393–400 (1965)). U.S. Pat. No. 3,278,378 describes fermentation methods for producing lysostaphin from culture media of S. staphylolyticus, later renamed S. simulans. Other methods for producing lysostaphin are further described in U.S. Pat. Nos. 3,398,056 and 3,594,284. The gene forlysostaphin has subsequently been cloned and sequenced (Recsei et al., Proc. Natl. Acad. Sci. USA, 84: 1127–1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62–68 (1968)). Lysostaphin, in combination with the lysin enzyme, can be used in the presence or absence of the listed antibiotics. There is a degree of added importance in using both lysostaphin and the lysin enzyme in the same therapeutic agent. Frequently, when a body has a bacterial infection, the infection by one genus of bacteria weakens the body or changes the bacterial flora of the body, allowing other potentially pathogenic bacteria to infect the body. One of the bacteria that sometimes co-infects a body is Staphylococcus aureus. Many strains of Staphylococcus aureus produce penicillinase, such that both the Staphylococcus and the Streptococcus strains will not be killed by standard antibiotics. Consequently, the use of the lysin and lysostaphin, possibly in combination with antibiotics, can serve as the most rapid and effective treatment of bacterial infections. In yet another preferred embodiment, the invention may include mutanolysin, and lysozyme.

While this treatment may be used in any mammalian species, the preferred use of this product is for a human.

Many modifications and variations of the present invention are possible in light of the above teachings. It is, therefore, to be understood within the scope of the appended claims the invention may be protected otherwise than as specifically described.

What is claimed is:

1. A method for the treatment of dermatological streptococcal infections comprising:
   administering to an infected area of the body a composition comprising effective amount of a therapeutic agent, said therapeutic agent comprising a lysin enzyme produced by group C streptococcal bacteria infected with a C1 bacteriophage.

2. The method according to claim 1, further comprising delivering said therapeutic agent in a pharmaceutically acceptable carrier.

3. The method according to claim 2, wherein said carrier is selected from the group consisting of an aqueous liquid, an alcohol base, a water soluble gel, a lotion, an ointment, a nonaqueous liquid base, a mineral oil base, a blend of mineral oil and petrolatum, lanolin, liposomes, hydrophilic gelling agents, cross-linked acrylic acid polymers, cellulose polymers, hydroxy ethyl cellulose, cellulose gum, MVE/MA decadiene crosspolymers, PVM/MA copolymers, and any combinations thereof.

4. The method according to claim 1, wherein the form in which the composition is delivered is selected from the group consisting of a spray, a smear, a time release patch, a liquid absorbed wipe, and any combinations thereof.

5. The method according to claim 1, wherein the lysin enzyme is in an environment having a pH which allows for activity of said lysin enzyme.

6. The method according to claim 5, wherein said composition further comprises a buffer that maintains pH of the composition at a range between about 4.0 and about 9.0.

7. The method according to claim 6, wherein said buffer maintains the pH of the composition at the range of between about 5.5 and about 7.5.

8. The method according to claim 6, wherein said buffer comprises a reducing agent.

9. The method according to claim 8, wherein said reducing agent is dithiothreitol.

10. The method according to claim 6, wherein said buffer comprises a metal chelating reagent.

11. The method according to claim 10, wherein said metal chelating reagent is ethylenediaminetetraacetic disodium salt.

12. The method according to claim 6, wherein said buffer is a citrate-phosphate buffer.

13. The method according to claim 6, further comprising a bactericidal or bacteriostatic agent as a preservative.

14. The method according to claim 1, wherein the therapeutic agent further comprises a mild surfactant in an amount effective to potentiate the therapeutic effect of the lysin enzyme.

15. The method according to claim 1, wherein the therapeutic agent further comprises at least one complementary agent which potentiates the bactericidal activity of the lysine enzyme, said complementary agent being selected from the group consisting of penicillin, synthetic penicillins bacitracin, methicillin, cephalosporin, polymyxin, cefaclor, Cefadroxil, cefamandole nafate, cefazolin, cefixime, cefinetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and chelating agents in an amount effective to synergistically enhance the therapeutic effect of the lysin enzyme.

16. The method according to claim 1, wherein the therapeutic agent further comprises lysostaphin for the treatment of any *Staphylococcus aureus* bacteria.

17. The method according to claim 1, wherein the therapeutic agent further comprises mutanolysin.

18. The method according to claim 1, wherein the therapeutic agent further comprises lysozyme.

19. The method according to claim 1, wherein said lysin enzyme is present in an amount ranging from about 100 to about 500,000 units per milliliter.

20. The method according to claim 19, wherein said lysin enzyme is present in an amount ranging from about 1,000 units to about 100,000 units per milliliter.

21. The method according to claim 20, wherein said lysin enzyme is present in an amount ranging from about 10,000 units to about 100,000 units per milliliter.

22. A composition for the treatment of dermatological streptococcal infections comprising:
    an effective amount of a therapeutic agent, said therapeutic agent comprising a lysin enzyme produced by group C streptococcal bacteria infected with a C1 bacteriophage, and
    a pharmaceutically acceptable carrier for topical application of the lysin enzyme.

23. The composition according to claim 22, wherein said carrier is selected from the group consisting of an aqueous liquid, an alcohol base, a water soluble gel, a lotion, an ointment, a nonaqueous liquid base, a mineral oil base, a blend of mineral oil and petrolatum, lanolin, liposomes, hydrophilic gelling agents, cross-linked acrylic acid polymers, cellulose polymers, hydroxy ethyl cellulose, cellulose gum, MVE/MA decadiene crosspolymers, PVMM copolymers, and any combinations thereof.

24. The composition according to claim 22, wherein said composition is in the form selected from the group consisting of a spray, a smear, a time release patch, a liquid absorbed wipe, and any combinations thereof.

25. The composition according to claim 22, wherein the lysin enzyme is in an environment having a pH which allows for activity of said lysin enzyme.

26. The composition according to claim 20, wherein said composition further comprises a buffer that maintains pH of the composition at a range between about 4.0 and about 9.0.

27. The composition according to claim 26, wherein said buffer maintains the pH of the composition at the range of between about 5.5 and about 7.5.

28. The composition according to claim 26, wherein said buffer comprises a reducing agent.

29. The composition according to claim 28, wherein said reducing agent is dithiotlireitol.

30. The composition according to claim 26, wherein said buffer comprises a metal chelating reagent.

31. The composition according to claim 30, wherein said metal chelating reagent is ethylenediaminetetraacetic disodium salt.

32. The composition according to claim 26, wherein said buffer is a citrate-phosphate buffer.

33. The composition according to claim 22, further comprising a bactericidal or bacteriostatic agent as a preservative.

34. The composition according to claim 22, further comprising a surfactant in an amount effective to potentiate the therapeutic effect of the therapeutic agent.

35. The composition according to claim 22, wherein the therapeutic agent further comprises at least one complementary agent which potentiates the bactericidal activity of the lysine enzyme, said complementary agent being selected from the group consisting of penicillin, synthetic penicillins bacitracin, methicillin, cephalosporin, polymyxin, cefaclor, Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef, mafate chelating agents, and combinations thereof in an amount effective to synergistically enhance the therapeutic effect of the lysin enzyme.

36. The composition according to claim 22, wherein the therapeutic agent further comprises lysostaphin for the treatment of any *Staphylococcus aureus* bacteria.

37. The composition according to claim 22, wherein the therapeutic agent further comprises mutanolysin.

38. The composition according to claim 22, wherein the therapeutic agent further comprises lysozyme.

39. The composition according to claim 22, wherein said lysin enzyme is present in an amount ranging from about 100 to about 500,000 units per milliliter.

40. The composition according to claim 22, wherein said lysin enzyme is present in an amount ranging from about 1,000 units to about 100,000 units per milliliter.

41. The composition according to claim 22, wherein said lysin enzyme is present in an amount ranging from about 10,000 units to about 100,000 units per milliliter.

42. The composition according to claim 22, further comprising at least one emulsifier.

43. The composition according to claim 22, further comprising at least one antioxidant.

44. The composition according to claim 22, further comprising at least one sunscreen.

45. The composition according to claim 22, further comprising at least one preservative.

46. The composition according to claim 22, further comprising at least one anti-inflammatory agent.

47. The composition according to claim 22, further comprising at least one local anesthetic.

48. The composition according to claim 22, further comprising at least corticosteroid.

49. The composition according to claim 22, further comprising at least one destructive therapy agent.

* * * * *